United States Patent [19]

Malpass et al.

[11] 4,113,783
[45] Sep. 12, 1978

[54] REDUCTION OF TRIPHENYLPHOSPHINE OXIDE TO TRIPHENYLPHOSPHINE

[75] Inventors: Dennis B. Malpass, LaPorte; G. Scott Yeargin, Pasadena, both of Tex.

[73] Assignee: Texas Alkyls, Inc., Deer Park, Tex.

[21] Appl. No.: 805,194

[22] Filed: Jun. 9, 1977

Related U.S. Application Data

[63] Continuation-in-part of Ser. No. 686,978, May 17, 1976, abandoned.

[51] Int. Cl.$^2$ .............................................. C07F 9/50
[52] U.S. Cl. .............................................. 260/606.5 P
[58] Field of Search .................................. 260/606.5 P

[56] References Cited

U.S. PATENT DOCUMENTS

| | | | |
|---|---|---|---|
| 3,518,303 | 6/1970 | Maier | 260/606.5 P X |
| 3,780,111 | 12/1973 | Young et al. | 260/606.5 P |
| 4,053,521 | 10/1977 | Giongo et al. | 260/606.5 P X |

OTHER PUBLICATIONS

Schindler et al., Angew. Chem. Internat. Ed. V4, p. 153 (1965).
Issleib et al., Z. Anory. Allgem. Chem. 299, 58–68 (1959).
Koster et al., Agnew. Chem. V77, pp. 589, 590 (1965).
Mole et al., Organoaluminum Compounds, Elsevier Publ. Co., N. Y., pp. 55 & 56 (1972).
Kosolapoff, Organic Phosphorus Compounds, V1, pp. 45 to 47 (1972).
Kosolapoff, Organic Phosphorus Compounds, V3, pp. 408 to 416 (1972).

*Primary Examiner*—Helen M. S. Sneed
*Attorney, Agent, or Firm*—M. Henry Heines

[57] ABSTRACT

Triphenylphosphine oxide is reduced to triphenylphosphine by the steps of
(a) reacting triphenylphosphine oxide with a dialkylaluminum hydride either formed externally to the reaction system or generated in situ by the application of heat to a trialkylaluminum in which at least one alkyl group contains from 2 to 15 carbon atoms and in which the $\beta$-carbon on said alkyl group is directly bonded to at least one hydrogen atom, and
(b) hydrolyzing the product of step (a) to produce triphenylphosphine.

17 Claims, No Drawings

REDUCTION OF TRIPHENYLPHOSPHINE OXIDE TO TRIPHENYLPHOSPHINE

CROSS REFERENCE TO RELATED APPLICATIONS

This is a continuation-in-part of copending application Ser. No. 686,978, filed May 17, 1976, now abandoned.

SUMMARY OF THE INVENTION

This invention relates to a novel process for the reduction of triphenylphosphine oxide to triphenylphosphine. Triphenylphosphine is well known as a useful reagent in a wide variety of processes. Notable among these are processes involving the Wittig reaction wherein, e.g., a ketone or an aldehyde group is converted into an olefin linkage. The Wittig reaction has wide use in the synthesis of Vitamins A and E, and produces the by-product triphenylphosphine oxide by oxidation of triphenylphosphine. As an important factor in the economics of the Wittig reaction, the triphenylphosphine oxide is subsequently reduced to triphenylphosphine for recycling. The present invention relates to a process for achieving this reduction economically to result in a product of a high degree of purity.

BACKGROUND OF THE INVENTION

Numerous methods are known in the art for the reduction of triphenylphosphine oxide to triphenylphosphine, all of which entail either expense, complex reaction mechanisms, reagent handling problems, or other problems. Examples of such methods are the use of inorganic and organic silicone compounds with tertiary amines (U.S. Pat. No. 3,261,871), and the use of metals or metal aluminum hydrides in the presence of a silicone halide (U.S. Pat. No. 3,280,195). Other processes involve the use of a halo complexing agent to form an adduct of triphenylphosphine oxide, which is then heated to decomposition temperature to form the triphenylphosphine dihalide, which is subsequently reduced with a metal reducing agent (U.S. Pat. No. 3,405,180) or with iron with an oxidation potential of 0.44 volt (U.S. Pat. No. 3,780,111). In view of the complexity of the above methods, a simplified and inexpensive process which will yield a product of high purity is highly desirable.

The reducing agent diisobutylaluminum hydride is described in a sales brochure entitled "Specialty Reducing Agents," prepared by Texas Alkyls, Inc. (available through Stauffer Chemical Company, Westport, Conneticut 06880), published in April 1971. A table on page 15 of the brochure lists anticipated yields of various reduction reactions using diisobutylaluminum hydride. Among the entries in the table is a figure representing the triphenylphosphine oxide reaction. Subsequent to the publication of the brochure, actual experiments were run. The results, which are shown hereinbelow, prove that the quoted figure for the triphenylphosphine oxide reduction is unobtainable at the indicated reactant ratio. In thus teaching results which are unobtainable, as the data hereinbelow will show, the brochure is an inoperative disclosure of this particular use of the reagent. Furthermore, the description in the brochure indicates no preference between aliphatic and aromatic solvents, beyond stating that for many reductions, an aromatic solvent is preferred to insure the solubility of the species to be reduced (page 6 of the brochure).

BRIEF DESCRIPTION OF THE INVENTION

In the practice of the present invention, triphenylphosphine oxide is reacted with a dialkylaluminum hydride, and the resulting product is hydrolyzed to give triphenylphosphine. The dialkylaluminum hydride can either be formed externally to the reaction system or be generated in situ by the application of heat to a trialkylaluminum which is capable of eliminating an olefin to form a dialkylaluminum hydride.

DETAILED DESCRIPTION OF THE INVENTION

The process of the present invention occurs in two steps: (a) the reduction of triphenylphosphine oxide with a dialkylaluminum hydride, followed by (b) the hydrolysis of the product of step (a) to give triphenylphosphine. These steps may either be carried out in the same vessel or in separate vessels. Furthermore, the hydrolysis step may be performed immediately after the reduction step or after a period of time has elapsed following the reduction step. The steps must not be performed simultaneously in the same vessel, because dialkylaluminum hydrides react vigorously with hydroxylic compounds such as water, alcohols, or carboxylic acids.

Neither the temperature nor the pressure at which the reduction reaction is performed nor the order of adding the reactants are essential to the process of the invention. Although the temperature is primarily limited by the melting and boiling points of the solvent used, it is generally convenient to run the reaction at a temperature between about 20° C. and about 140° C. The most preferred temperature range is between about 60° C. and about 130° C. Likewise, it will be convenient to use approximately atmospheric pressure.

The alkyl groups in the dialkylaluminum hydride can be the same or different and can each contain from 1 to 15 carbon atoms in a straight or branched chain. Straight- or branched-chain alkyl groups having from 1 to 5 carbon atoms are preferred. The most preferred dialkylaluminum hydride is diisobutylaluminum hydride.

The dialkylaluminum hydride can either be formed externally to the reaction system by any conventional means known in the art or generated in situ from a trialkylaluminum. The only trialkylaluminums which will generate a dialkylaluminum hydride in situ are trialkylaluminums which will generate a dialkylaluminum hydride in situ are trialkylaluminums in which at least one of the alkyl groups contains a minimum of two carbon atoms and a minimum of one hydrogen atom directly bonded to a β-carbon atom. A β-carbon atom is any carbon atom which is directly bonded to the carbon atom which is directly bonded to the aluminum atom. The dialkylaluminum hydride is formed from the trialkylaluminum by elimination of an olefin from the latter, which can only occur with a trialkylaluminum of the above-described structure. Thus, trimethylaluminum and tri-neopentylaluminum will not work in the present process.

The in situ generation of a dialkylaluminum hydride from a trialkylaluminum as defined above occurs by heating the reaction mixture containing the trialkylaluminum to a temperature between about 50° C. and 175° C., preferably from about 100° C. to about 150° C.

Although the particular mole ratio of the reactants used in the reduction step is not essential to the process of the invention, the extent of conversion of triphenylphosphine oxide to triphenylphosphine becomes greater as the mole ratio of the dialkylaluminum hydride to the triphenylphosphine oxide is increased. The best results will be obtained when this mole ratio is greater than or equal to about 1.0. A mole ratio between about 1.0 and about 5.0 is the most preferred.

The reduction reaction can be performed with or without a solvent. If a solvent is desired, any aliphatic or aromatic solvent can be used. It has been discovered, however, that a distinct advantage is gained by the use of aliphatic solvents rather than aromatic solvents. This advantage arises from the fact that triphenylphosphine is highly soluble in aliphatic solvents while triphenylphosphine oxide is much less soluble. As a result of this solubility difference, most of the unreduced triphenylphosphine oxide precipitates during the hydrolysis of step (b) of the process of the invention, while the sought-after triphenylphosphine remains dissolved in the aliphatic solvent. This result, which is much more highly pronounced with aliphatic rather than aromatic solvents, allows a product of substantially higher purity to be obtained. Consequently, recovery operations following the hydrolysis step are simplified, and an economic advantage is gained thereby. For this reason, aliphatic solvents are preferred over aromatic solvents. The most preferred aliphatic solvents are those containing 6 to 8 carbon atoms, inclusive.

As stated above, the product of the reduction reaction of step (a) is a complex consisting of triphenylphosphine and an aluminum oxide species. In the hydrolysis of step (b), this complex is hydrolyzed to produce triphenylphosphine, aluminum hydroxide and isobutane.

The hydrolysis reaction is strongly exothermic, and the heat of reaction can be removed by any conventional means, e.g., a cooling bath or cooling coils. Since the reaction produces gaseous isobutane, the temperature at which the reaction is performed is primarily limited by the ease with which the escaping gas is controlled. Although the reaction can be performed at temperatures close to the freezing point of the solution, the isobutane generated during the reaction at such low temperatures will be retained in solution until the temperature is allowed to rise. At high temperatures the generated isobutane escapes vigorously and creates a foam which is difficult to control. The preferred temperature range for the reaction is from about $-10°$ C. to about $+20°$ C. Similar to the reduction reaction, the particular pressure at which the hydrolysis is carried out is not essential to the reaction. Approximately atmospheric pressure is generally the most convenient.

The reaction mixture forms two liquid phases and possibly a solid precipitate consisting mainly of triphenylphosphine oxide, depending on the type and amount of solvent used and the temperature of the solution. The upper liquid phase is the organic phase, and contains therein the desired product, triphenylphosphine. The lower liquid phase is the aqueous phase and contains the by-product aluminum hydroxide. It is preferred that the hydrolysis be carried out in the presence of a strong base in order that the aluminum species be transformed into an aluminum salt which is soluble in the aqueous phase. If water is used alone for the hydrolysis, the aluminum species will be in the form of a gel in the aqueous phase, creating handling problems. The strong base can be any water soluble base resulting in a solution of pH of at least about 10. An example of such a base is a 10 or 20 weight percent caustic solution, which, when combined with the aluminum hydroxide, forms sodium aluminate which will reside in solution in the aqueous phase.

At the completion of the hydrolysis reaction of step (b), the desired product can be recovered from the organic phase by any conventional recovery technique, for example, evaporation or distillation. Additional product can also be recovered from the solid precipitate when such a precipitate is formed. This can be achieved by extraction with an aromatic or an aliphatic solvent, followed by recovery of the desired product from the solvent. Subsequent to the recovery operation, unreacted triphenylphosphine oxide can be recycled back to the feed to the reduction reaction of step (a).

The following examples are offered to further illustrate the process of the invention.

EXAMPLE 1

A 500 ml, three-neck flask equipped with a silicone oil-cooled reflux condenser, a thermometer well, and a 50 ml addition funnel was purged with dry nitrogen under slight pressure. The flask was charged with 140 g of dry heptane and 30 g (0.108 mole) of triphenylphosphine oxide (TPPO). The mixture was heated to reflux (99° C.) over a magnetic stirrer/hotplate and 46.4 g (0.326 mole) of diisobutylaluminum hydride (DIBAL-H) was added over a period of 30 minutes. The mixture was then heated at reflux for 2 hours, and subsequently cooled to room temperature. Then, over a period of 1 hour, the mixture was added to a solution of 20 g NaOH in 100 g water and several cubes of ice. Two liquid phases and an undissolved solid (unreacted TPPO) resulted. The phases were separated and the clear organic (upper) phase was decanted from the solid. The solid was then washed with 25 ml heptane, which was then decanted and added to the original organic phase. The combined solvent portions were washed with 25 ml water and then evaporated to yield 23 g (0.877 mole) of TPP, or 81.4% yield, with melting point 69–76° C. and no impurities measurable by gas chromatography.

The following table lists a summary of the results of the above experiment (second entry) as well as those of additional experiments, spanning a variety of solvents and a range of DIBAL-H:TPPO mole ratios. The data in the table indicate that the purity of the product in area per cent is substantially improved when an aliphatic solvent is used rather than an aromatic solvent. The table also indicates that the yield obtainable with a mole ratio of 1.5 was less than 55% by interpolation between the two benzene entries, 46% by interpolation between the two toluene entries, and 48% by actual trial with heptane. The interpolations are based on the assumption that the relationship between yield and DIBAL-H:TPPO mole ratio is approximately linear. This assumption is corroborated by the heptane data. None of the yields for a 1.5 mole ratio, interpolated or actual, compare with the 78% yield quoted in the brochure mentioned in the Background of the Invention above. To the contrary, the table indicates that a mole ratio of close to 3.0 is necessary to achieve this result.

EXAMPLE 2

This example is offered to show the use of diisobutylaluminum hydride generated in situ by thermal treatment of triisobutylaluminum hydride.

A 250 ml reaction flask was charged with 5.0 g (0.0180 mole) of dry triphenylphosphine oxide (TPPO), 12.2 g (0.0615 mole) triisobutylaluminum (TIBAL) and 33.2 g of dry n-octane. Temperature of the reaction flask contents was raised to 125° C. maximum and was held in the range of 114° to 125° C. for three hours.

The reaction mixture from the above procedure was slowly added to a cold, aqueous 20% solution of sodium hydroxide. Upon cessation of gas evolution, the organic and aqueous phases were separated. The organic phase was washed with 50 ml water. The aqueous phase was washed with 16 g of benzene. The organic phase and benzene extract were combined.

Anaylsis of the combined organic mixture by gas chromatography showed only triphenylphosphine, n-octane, and benzene. No detectable amount of TPPO remained.

TABLE

REDUCTION OF TPPO TO TPP WITH DIBAL-H

| REACTANTS | | | | Reaction Temp. (° C) During DIBAL-H Addition$^a$ | PRODUCT - TPP | | |
|---|---|---|---|---|---|---|---|
| DIBAL-H Moles | TPPO Moles | Mole Ratio | Solvent | | Purity- Area % | Approximate Yield %$^b$ | Melting Range °C |
| Aliphatic Solvents: | | | | | | | |
| 4.183 | 1.394 | 3.00 | heptane | 23–108$^c$ | 92.3 | 81 | 67–72 |
| 0.326 | 0.108 | 3.03 | heptane | 23–101 | 100$^d$ | 81 | 69–76 |
| 0.215 | 0.108 | 1.99 | heptane | 23–101 | 95.5 | 59 | 70–73 |
| 0.214 | 0.108 | 1.98 | heptane | 23–101$^e$ | 90.6 | 47 | 69–75 |
| 0.161 | 0.108 | 1.49 | heptane | 23–101 | 93.5 | 48 | 64–74 |
| 0.114 | 0.108 | 1.06 | heptane | 23–101 | 91.3 | 30 | 65–70 |
| 0.030 | 0.011 | 2.83 | hexane | 23–69 | 100$^d$ | 72 | 71–80 |
| Aromatic Solvents: | | | | | | | |
| 0.061 | 0.020 | 3.00 | toluene | 23–78 | 87.5 | 71 | |
| 0.112 | 0.109 | 1.08 | toluene | 23–78 | 41.5 | 39 | 68–73 |
| 0.215 | 0.108 | 2.00 | benzene | 23–81 | 73.6 | 71 | 77–83 |
| 0.115 | 0.108 | 1.06 | benzene | 23–81 | 46.9 | 40 | 79–55 |
| Other: | | | | | | | |
| 0.113 | 0.108 | 1.05 | Et$_2$O | 36 | 39.2 | 35 | 70–75 |
| 0.037 | 0.036 | 1.03 | none | 23–75$^f$ | 98.4 | 43 | 75–80 |

$^a$Unless otherwise noted, DIBAL-H was added over a period of 30–45 minutes, and the reaction mixture was refluxed for 2 hours thereafter.
$^b$Determined by multiplying weight of product by purity, converting to moles of TPP, and dividing by moles of original TPPO.
$^c$DIBAL-H added over period of 3 hours.
$^d$Impurities not detectable by gas chromatography.
$^e$Reaction mixture refluxed for 5 hours after addition of DIBAL-H.
$^f$Reaction mixture maintained at 75° C for 2 hours after addition of DIBAL-H.

What is claimed is:

1. A process for the conversion of triphenylphosphine oxide to triphenylphosphine comprising the steps of
   (a) reacting triphenylphosphine oxide with a dialkyl-aluminum hydride of which the alkyl groups are the same or different and each contain from 1 to 15 carbon atoms in a straight or branched chain; and
   (b) hydrolyzing the product of step (a).

2. The process of claim 1 in which the alkyl groups in the dialkylaluminum hydride of step (a) are the same or different and each contain from 1 to 5 carbon atoms in a straight or branched chain.

3. The process of claim 1 in which the dialkylaluminum hydride of step (a) is diisobutylaluminum hydride.

4. The process of claim 1 in which the reaction of step (a) occurs in the presence of an aliphatic solvent.

5. The process of claim 4 in which the aliphatic solvent contains 6 to 8 carbon atoms, inclusive.

6. The process of claim 1 in which the reaction of step (a) occurs at a temperature between about 20° C. and about 140° C.

7. The process of claim 1 in which the reaction of step (a) occurs at a temperature between about 60° C. and about 130° C.

8. The process of claim 1 in which the reaction of step (a) occurs at approximately atmospheric pressure.

9. The process of claim 1 in which the mole ratio of dialkylaluminum hydride to triphenylphosphine oxide in step (a) is greater than about 1.0.

10. The process of claim 1 in which the mole ratio of dialkylaluminum hydride to triphenylphosphine oxide in step (a) is between about 1.0 and about 5.0.

11. The process of claim 1 in which step (b) is conducted at a temperature from about −10° C. to about +20° C.

12. The process of claim 1 in which step (b) is conducted in the presence of a base of pH of at least about 10.

13. The process of claim 1 in which step (b) is conducted at approximately atmospheric pressure.

14. The process of claim 1 in which triphenylphosphine is recovered from the product of step (b).

15. The process of claim 1 in which unreacted triphenylphosphine oxide is separated from the product of step (b) and recycled to step (a).

16. The process of claim 1 in which the dialkylaluminum hydride of step (a) is generated in situ by heating a trialkyl-aluminum in which one alkyl group contains a minimum of two carbon atoms and a minimum of one hydrogen atom directly bonded to a β-carbon atom, to a temperature between about 50° C. and about 175° C.

17. The process of claim 16 in which the trialkylaluminum is heated to a temperature between about 100° C. and about 150° C.

* * * * *